United States Patent
Gielen

(10) Patent No.: US 6,308,103 B1
(45) Date of Patent: Oct. 23, 2001

(54) SELF-CENTERING EPIDURAL SPINAL CORD LEAD AND METHOD

(75) Inventor: Frans L. H. Gielen, Eckelrade (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/394,317

(22) Filed: Sep. 13, 1999

(51) Int. Cl.$^7$ ........................................ A61N 1/05
(52) U.S. Cl. .............................. 607/117; 600/382
(58) Field of Search .................. 607/116–119, 122, 607/126; 600/373–375, 377, 378, 382

(56) References Cited

U.S. PATENT DOCUMENTS

| | | | |
|---|---|---|---|
| 4,141,365 | 2/1979 | Fischell et al. | 128/404 |
| 4,285,347 | 8/1981 | Hess | 128/785 |
| 4,519,403 * | 5/1985 | Dickhudt | 607/117 |
| 4,590,949 | 5/1986 | Pohndorf | 128/785 |
| 4,658,835 | 4/1987 | Pohndorf | 128/785 |
| 4,800,898 | 1/1989 | Hess et al. | 128/785 |
| 5,121,754 | 6/1992 | Mullett | 128/786 |
| 5,255,691 | 10/1993 | Otten | 607/117 |
| 5,417,719 | 5/1995 | Hull et al. | 607/117 |
| 5,501,703 | 3/1996 | Holsheimer et al. | 407/46 |
| 5,628,317 | 5/1997 | Starkebaum et al. | 128/660.03 |
| 5,643,330 | 7/1997 | Holsheimer et al. | 607/46 |
| 5,713,922 | 2/1998 | King | 607/2 |
| 5,733,322 | 3/1998 | Starkebaum | 607/117 |
| 6,161,047 * | 12/2000 | King et al. | 607/62 |

* cited by examiner

Primary Examiner—Jeffrey R. Jastrzab
(74) Attorney, Agent, or Firm—Thomas F. Woods; Tom G. Berry

(57) ABSTRACT

A self-centering epidural lead is configured to center itself in an optimal location in respect of the midline of the spinal cord for stimulation of the cord. A method for using the lead in spinal cord stimulation is also described. The self-centering epidural lead includes a front side configured to face the spinal cord and a back side to which a pivot member or other self-centering device is operably attached. The pivot member or other self-centering device stabilizes the lead in an optimal position adjacent the spinal cord and aids in preventing spatial migration of the lead.

1 Claim, 8 Drawing Sheets

SELF-CENTERING EPIDURAL SPINAL CORD LEAD AND METHOD

FIELD OF THE INVENTION

This invention relates to implantable techniques for electrical simulation of the spinal cord. More particularly, this invention relates to a lead implanted adjacent the spinal cord during such electrical stimulation which centers itself in respect of the midline of the spinal cord.

BACKGROUND OF THE INVENTION

Leads for electrical stimulation of a spinal cord, particularly those employed to induce paresthesia in areas of the body experiencing pain, are known in the art. Epidural electrical stimulation of the spinal cord has been shown to be effective in relieving certain types of pain. One approach to providing such stimulation is to introduce a transcutaneous lead directly into the epidural space overlying the spinal cord. Such leads may be chronically implanted into a patient adjacent to the spinal cord to provide continuous treatment for pain.

Over time, and particularly during the first two or three weeks following lead implant surgery, the position of alead with respect to the spinal cord may inadvertently change. Because of such displacement, the lead may not provide stimulation to the original target spinal area. Such positioning changes may impair the clinical benefit of the stimulation provided by the lead. One method disclosed in U.S. Pat. No. 3,636,940 to Timm et al. involves suturing the lead in place after implantation. Suturing adds to the time required to perform surgery and may have adverse effects on the implant site.

Selection of the stimulation site within the spinal cord is performed at implantation. The surgeon generally places the electrode either surgically or percutaneously at the exact position to be stimulated. The position is determined by providing test stimulations with the lead. Leads placed in a less than optimal position may contribute to disagreeable sensations or unintended involuntary motor responses in the patient. Thus, time and effort are necessary to place existing leads in the desired region of the spinal cord during implantation. Often, it is even more difficult and time-consuming to re-adjust leads that have migrated once the leads have been implanted in a patient's body. Moreover, leads that have migrated after surgery are also susceptible to causing side effects such as disagreeable sensations or unintended involuntary motor responses. In extreme cases, repositioning of leads using further surgery is required.

To limit the need for physically repositioning chronically implanted leads, some techniques have been developed to compensate for changing post-operative lead positions. One technique is to electronically select one or more electrodes to generate a pulse signal to tailor or direct the resulting stimulation pattern to a particular individual's painful body part site or region. Those methods can partly overcome the effects of small lead migrations and may minimize unwanted motor responses.

Despite the existence of such methods of compensation and correction, however, unpleasant physical sensations and reduced efficacy of stimulation can still result from lead migration.

A percutaneous lead designed to be implanted adjacent the spinal cord is discussed in U.S. Pat. No. 4,285,347 issued to Hess. The Hess lead employs a looped protrusion at the distal tip to stabilize the electrode's position. U.S. Pat. No. 5,121,754, and assigned to Medtronic, Inc., also provides a percutaneous lead with a deformable distal shape. The distal portion is held straight with a stylet during insertion into the epidural spinal canal. After placement, the stylet is removed and the bend deforms within the epidural space. Both of these leads are known to post-operatively migrate, however, to some extent, are shaped and configured at the time of implantation.

Other percutaneous leads and devices and methods employed include those disclosed in the U.S. Patents listed below in Table 1.

Table 1

U.S. Patent No. Title
U.S. Pat. No. 5,733,322 Positive fixation percutaneous epidural neurostimulation lead
U.S. Pat. No. 5,255,691 Percutaneous epidural lead introducing system and method
U.S. Pat. No. 5,205,828 Epidural needle location indicator assembly
U.S. Pat. No. 5,119,832 Epidural catheter with nerve stimulators
U.S. Pat. No. 5,081,990 Catheter for spinal epidural injection of drugs and measurement of evoked potentials
U.S. Pat. No. 5,058,584 Method and apparatus for epidural burst stimulation for angina pectoris
U.S. Pat. No. 4,808,157 Multi-lumen epidural-spinal needle
U.S. Pat. No. 4,467,800 Tool for creating a pocket for a epidural electrode
U.S. Pat. No. 4,383,532 Epidural lead advancer
U.S. Pat. No. 4,141,365 Epidural lead electrode and insertion needle The stimulation systems of U.S. Pat. Nos. 5,501,703; 5,628,317; 5,643,330, and 5,713,922 assigned to Medtronic, Inc. disclose a simplified surgical lead resembling a paddle as shown in cross-section in FIGS. 7 and 8. Those figures illustrate that such a paddle-like lead may tend to slip from its optimal or original position subsequent to implantation. Such slippage from the midline can occur because of several factors, including, general lead migration (as described above), lateral positioning during surgery, or an asymmetrical position of the patient's spinal cord within the canal. Adaptation of the lead itself to withstand lead migration or for aberrant positioning after implantation would therefore be beneficial.

As those of ordinary skill in the art will appreciate readily upon reading the Summary of the Invention, Detailed Description of the Preferred Embodiments and Claims set forth below, at least some of the devices and methods disclosed in the patents of Table 1 and referenced elsewhere herein may be modified advantageously in accordance with the teachings of the present invention.

SUMMARY OF THE INVENTION

The present invention overcomes at least some of the disadvantages described above by providing a lead apparatus for epidural spinal cord stimulation capable of centering itself in an optimal position over the midline of the spinal cord and by providing a lead whose structure allows it to be implanted (temporarily or chronically) within a patient without requiring additional readjustment of the lead's placement over the spinal cord.

Various embodiments of the lead of the present invention have one or more objects. That is, various embodiments of the present invention provide one or more solutions to certain problems existing in the prior art, such as: (a) reduced efficacy of stimulation when an epidural lead moves from its original implant position, and (b) unwanted side effects of stimulation such as involuntary motor responses or disagreeable sensations which result from the stimulation lead's migration.

Various embodiments of the lead of the present invention provide one or more advantages, including: (a) having the capability to center itself without further intervention (such as further surgical intervention), (b) having the capability to be tailored to an optimal epidural shape for placement in a specific patient, (c) being well suited for use in systems of stimulation that vary the pulse signal of stimulation.

Various embodiments of the lead of the present invention provide one or more features, including: (a) a pivot on a lead paddle capable of causing the lead paddle to center itself in an optimal location; (b) a lead paddle capable of carrying various configurations of electrodes, (especially configurations well-suited for systems of stimulation that vary the pulse signal of stimulation); (c) a member that may be inflated to an optimal epidural shape for placement in a specific patient; (d) an inflatable member that may be attached to a center region of the lead paddle of the present invention and that may be inflated fully or partially to the extent preferred to achieve a centering function; (e) an inflatable member formed of material such as silicon rubber and that may be formed integrally to the paddle, or separate therefrom, and then fastened to the paddle.

Methods of making and using the foregoing self-centering epidural spinal cord stimulation lead also fall within the scope of the present invention.

Other features, advantages and objects of the present invention will become more apparent by referring to the appended drawings, detailed description and claims.

DETAILED DESCRIPTION OF THE PREFERRED EMBODIMENTS

Figure 1:
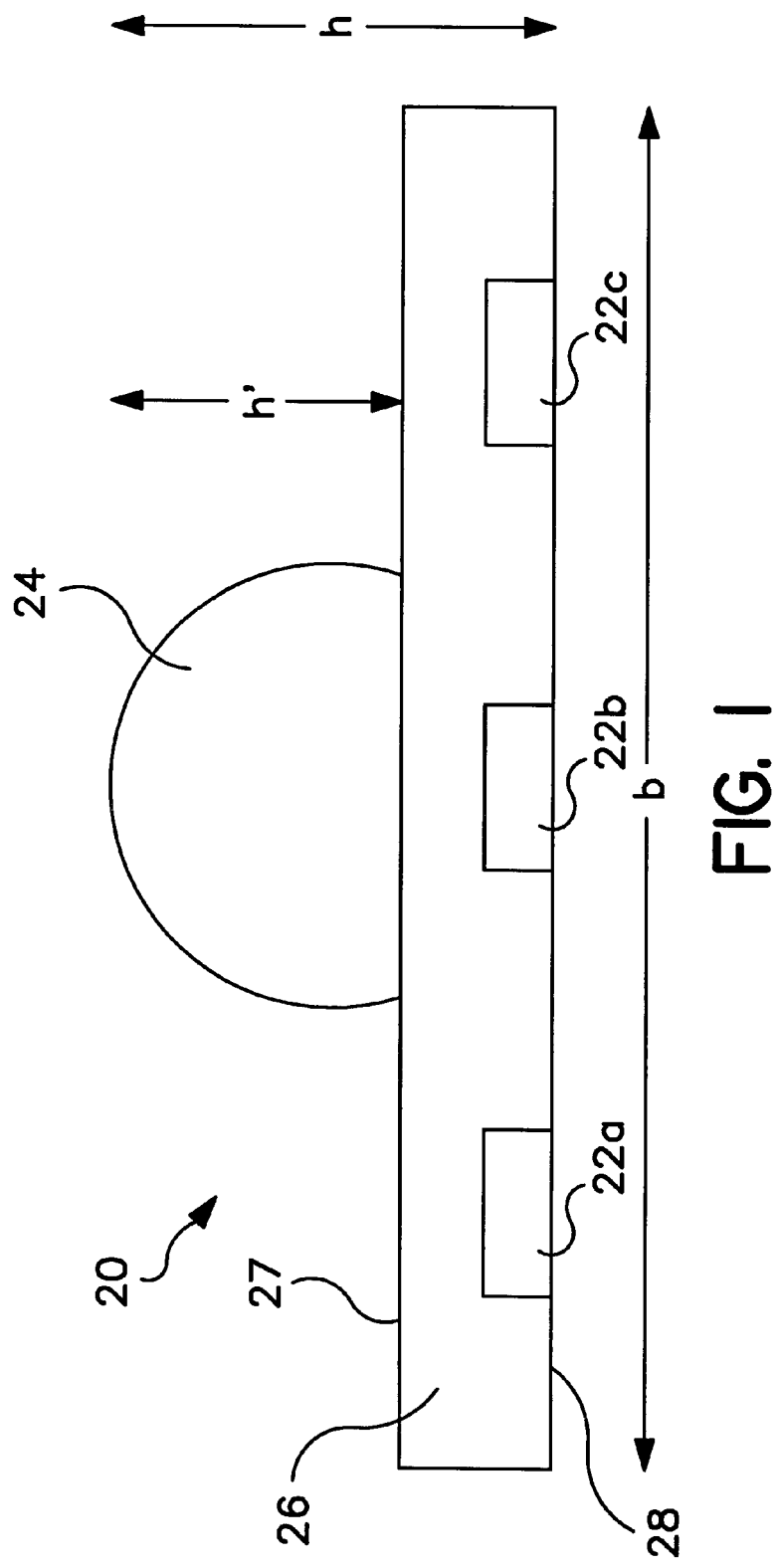
FIG. 1 is a sectional view of a first embodiment of a self-centering epidural lead of the present invention.
Figure 3:
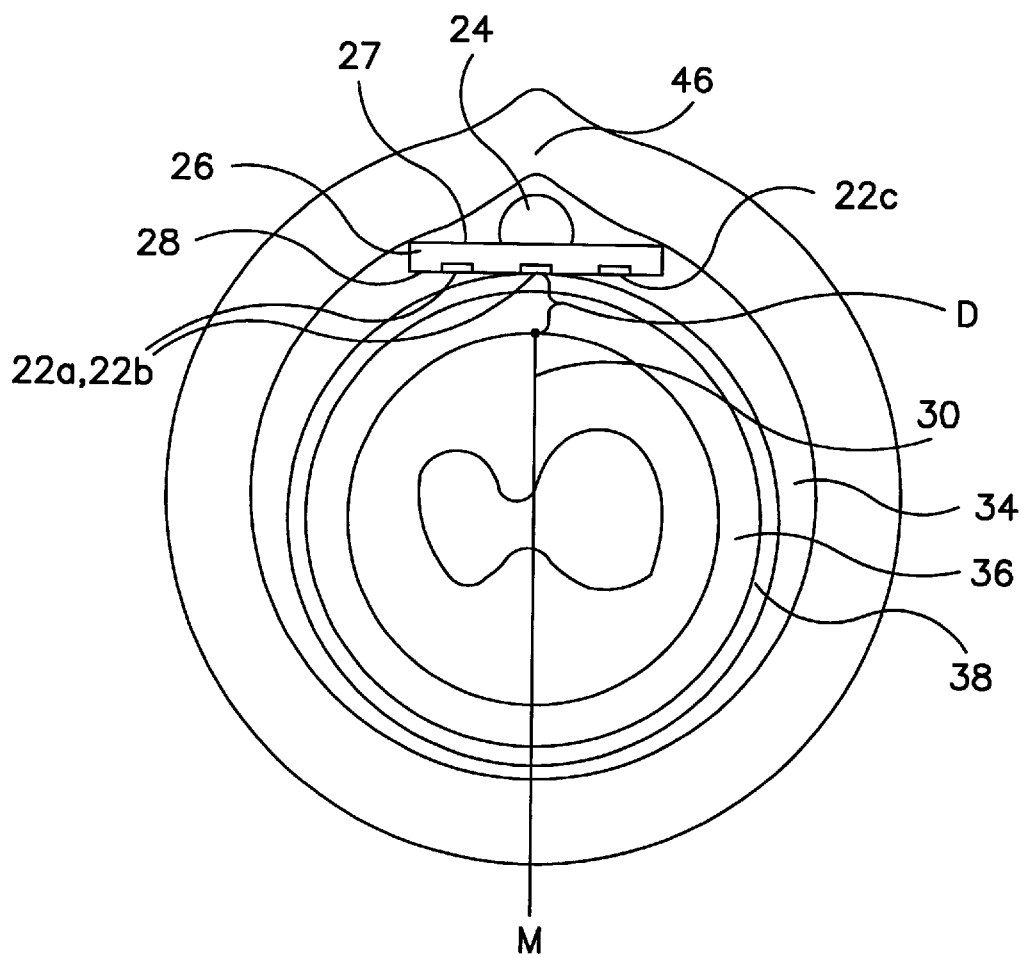
FIG. 3 is a cross-sectional view of the vertebral canal and the embodiment of FIG. 1 implanted in the epidural space.

A first embodiment of the self-centering epidural spinal cord lead is shown as numeral 20 in FIG. 1, and is also shown following implantation in a human body in FIG. 3. Such an embodiment comprises lead paddle 26 having front side 28 and back side 27. Lead paddle 26 is implanted so that front side 28 faces spinal cord 30. Pivot member 24 is operably attached to a center area of back side 27 of lead paddle 26.

Lead paddle 26 may also comprise one or more electrodes. As shown for example in the embodiment of FIG. 1, a plurality of electrodes 22a, 22b and 22c which are preferably arranged on front side 28 facing spinal cord 30, aligned along a common axis and in a generally planar configuration. However, electrodes 22a–22c may be arranged anywhere on or within lead paddle 26. Electrodes 22a–22c may furthermore preferably be arranged to establish a cathode/anode relationship although other electrode arrangements are possible.

Lead 20 may then be operably attached to a source of power that provides electrical stimulation to spinal cord 30 through electrodes 22a–22c.

The material comprising lead paddle 26 is preferably a biocompatible and biostable material suitable for implantation within a patient. Such materials are well known and prompt little allergenic response from the patient's body and are resistant to corrosion or degradation resulting from implantation within the patient's body. Furthermore, such a material should not cause any additional stress to the patient's body by, for example, not scraping detrimentally against any elements within spinal cord 30. In an illustrative embodiment, lead paddle 26 is made of biocompatible rubber. However, biocompatible, biostable plastic or other materials well known in the art may be used.

The same or similar biocompatible, biostable material can be used to form pivot member 24 as used to form lead paddle 26. The whole of lead 20 may be formed as a continuous piece. That is, lead paddle 26 and pivot member 24 may be formed as an integral member. Alternatively, lead paddle 26 may be formed separately from pivot member 24. Pivot member 24 would then be attached to lead paddle 26 by fastening means. Such fastening means would preferably be biocompatible materials such as fast curing biocompatible rubber or glue or biocompatible processes such as suturing. However, other fastening means known in the art may also be employed.

As shown in FIG. 3, lead 20 is inserted within epidural space 34 near dura mater 38 with front side 28 of lead paddle 26 facing spinal cord 30 and pivot member 24 extending into epidural space 34. Pivot member 24 may extend into space 34 as far as bony spinal canal 46 or may extend any distance towards bony spinal canal 46 less than the distance between bony spinal canal 46 and dura mater 38. Also shown for purposes of orientation is subdural space 36. It should be noted that the dorsal side of the spinal cord is that which corresponds to the back side of a typical vertebrate. In the case of FIG. 3 and FIGS. 5–8, the dorsal side is oriented towards the top of the figures.

Lead 20 may be inserted into epidural space 34 using existing tools and techniques for the insertion of leads into the spinal canal, such as, for example, percutaneous insertion. For chronic implantation, lead 20 may be inserted during surgery. Other known implantation and insertion techniques may be used. Although lead 20 may be inserted in other areas, the embodiment of FIG. 3 shows lead 20 being implanted near the dorsal surface of the spinal cord 30 adjacent the dura mater 38. The initial position and orientation of lead 20 can be monitored, for example, by radiographic monitors. Preferably, and as shown in the embodiment of the present invention shown in FIG. 3, lead 20 is implanted so that central electrode 22b faces midline M of spinal cord 30 and lead paddle 26 is centered in epidural space 34 between spinal cord 30 and bony spinal canal 46.

Figure 5:
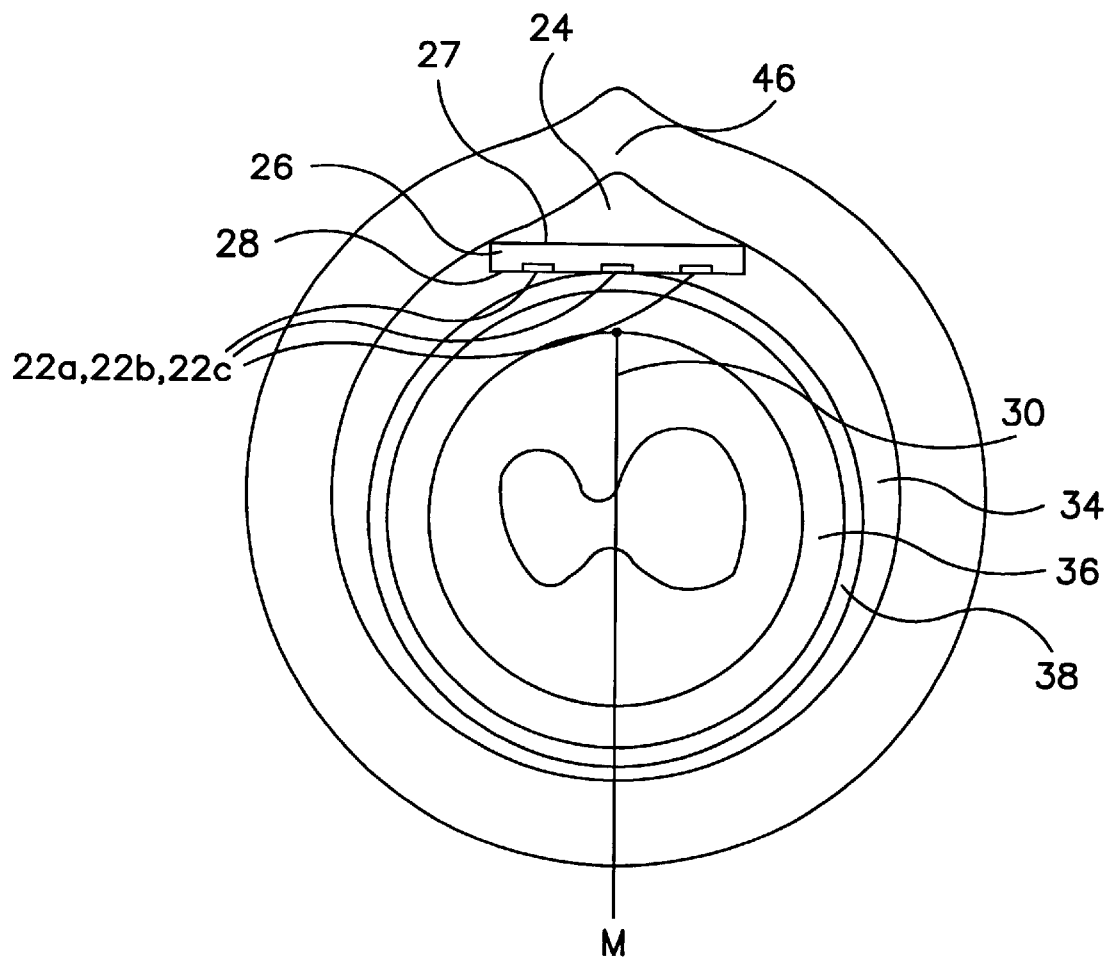
FIGS. 5 and 6 are cross-sectional views of the vertebral canal with alternative embodiments of FIG. 1 implanted in the epidural space.
Figure 6:
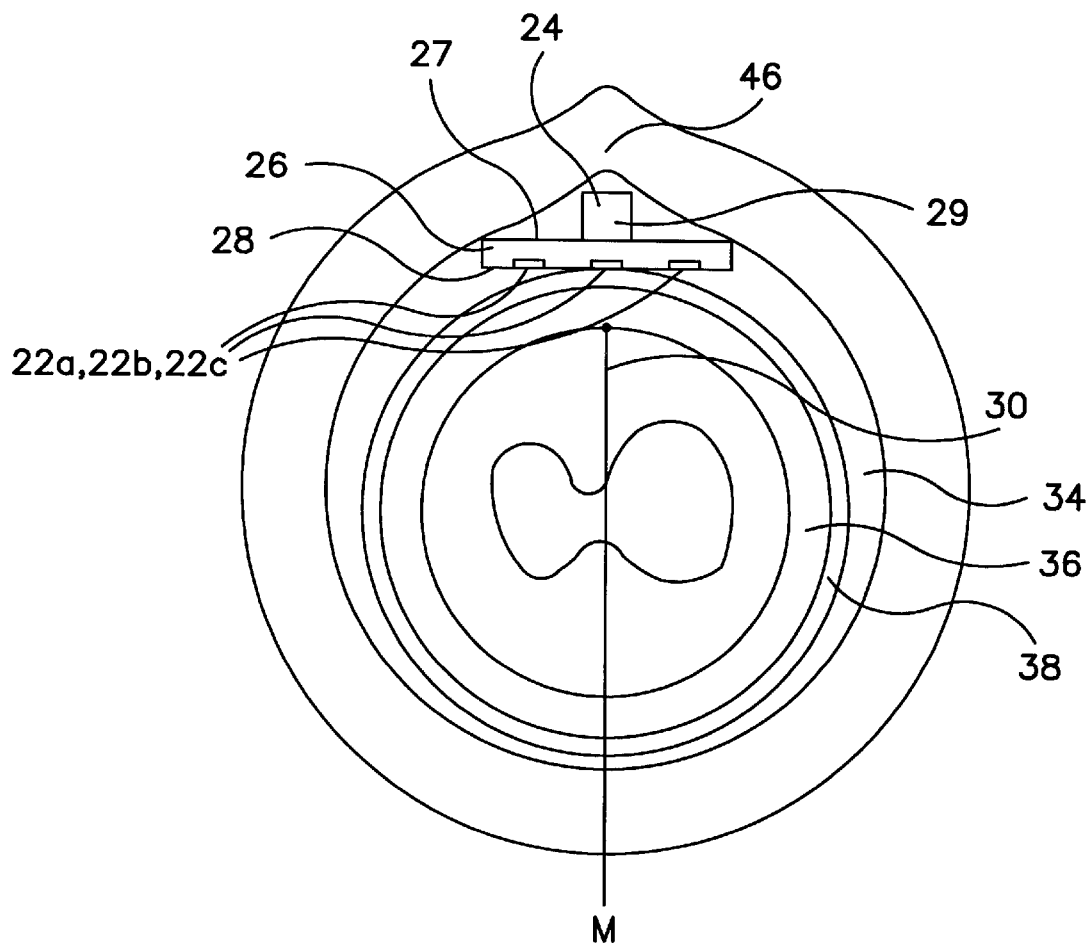

As shown in cross section in FIG. 1, pivot member 24 may have a curved shape. This shape may be a partial circle (FIG. 1) or any other curved shape, including a shape having a spherical radius or a shape having a more tapered point (as shown in FIG. 3). The shape of the pivot may be of any configuration that is suitable to achieve the centering function. For example, two other possible configurations are shown in FIGS. 5 and 6. Preferably, the shape of pivot member 24 may conform to the slightly tapered shape of the bony spinal canal 46 of spinal cord 30.

As seen in FIG. 1, lead paddle 26 has a given width b. The combination of lead paddle 26 and pivot member 24 has a given height h, which includes height h' of pivot member 24. Preferably, height h' of pivot member 24 attached to lead paddle 26 would not exceed width b. In one embodiment height h' of pivot member 24 attached to lead paddle 26 might equal 0.5 b. In this embodiment of the present invention, if width b of lead paddle 26 is, for example, 2 mm, height h' of pivot member 24 attached to lead paddle 26 is 1 mm and height h may be, for example, 2 mm. In a preferred embodiment of the present invention, height h' is greater than 0.5 mm and less than 1 mm. However, height h' of pivot member 24 attached to lead paddle 26 may vary with such factors as the size of paddle 26, the length of paddle 26 and the shape of epidural space 34.

As seen in FIG. 1, lead 20 has a given height h which includes the height of lead paddle 26 and height h' of pivot member 24. Preferably height h of lead 20 does not exceed width b. For example, in the foregoing embodiment of the present invention, width b of lead paddle 26 is 2 mm. If height h' is 0.5 b (in this case, 1 mm), then height h of lead 20 is preferably 1 b (in this case, 2 mm). A preferred range for the value of h is $0.5\ b < h < 1.0\ b$. However, height h of lead 20 may vary with such factors as the size of paddle 26, the length of paddle 26 and the shape of epidural space 34.

Figure 4:
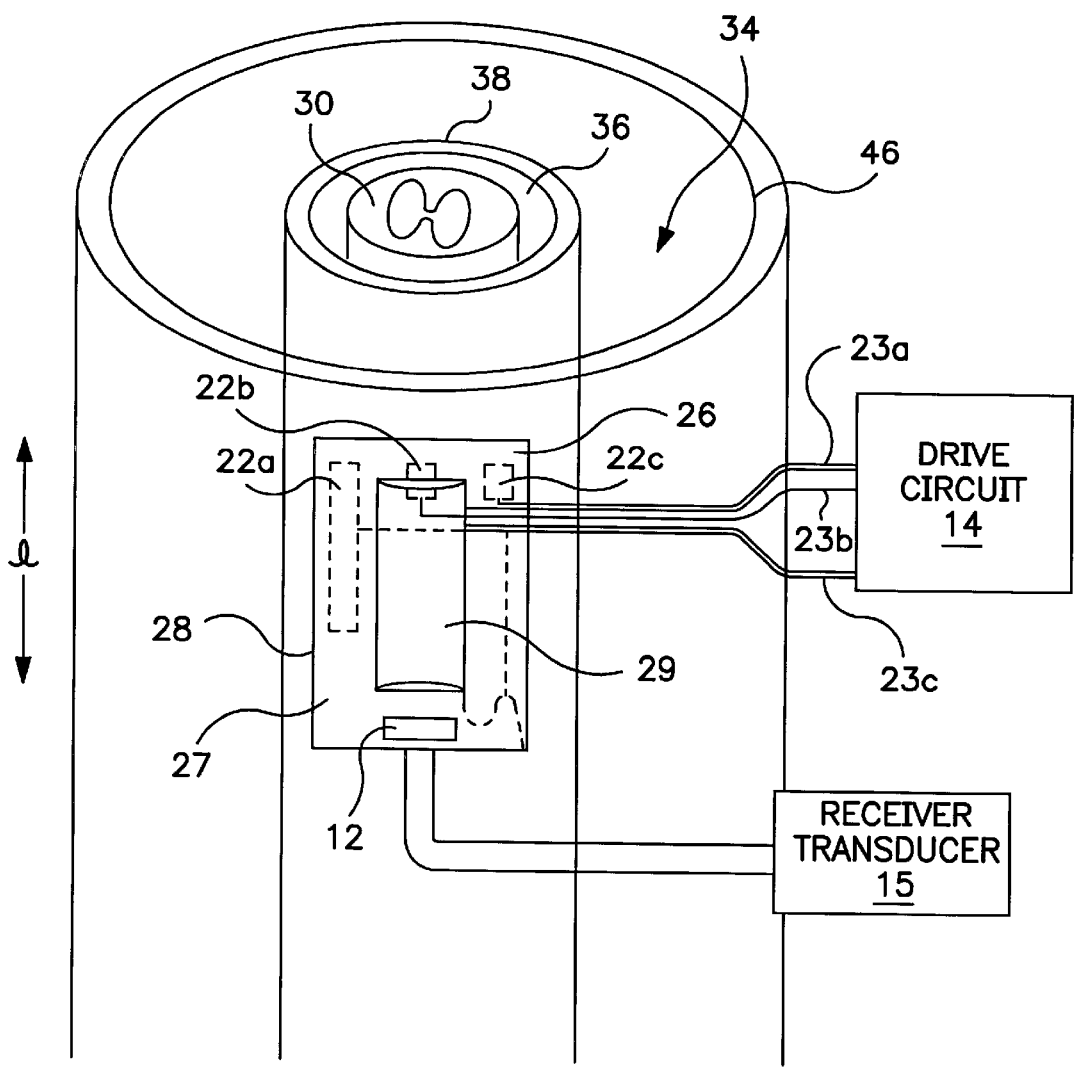
FIG. 4 is a back view of the embodiment of FIG. 1 implanted in the epidural space.

Referring now to FIG. 4, length L of lead paddle 26 is shown. Lead paddle 26 may be any length reasonable for implantation adjacent the spinal cord 30. A typical human spinal cord is approximately 500 mm in length, so length L of lead paddle 26 is preferably less than 50 mm. A preferred range for length L is $40\ mm \leq L \leq 50\ mm$. Preferably, length L' of pivot member 24 does not exceed length L' of lead 20. However, and as with lead paddle 26, length L' of pivot member 24 may be any length reasonable to accommodate implantation adjacent spinal cord 30. Depending on the needs of an individual patient, one or more such leads 20 may be inserted along the length of the spinal cord. As shown in shadow in FIG. 4, electrodes 22a, 22b and 22c can be of any configuration or shape.

In an optimal configuration of the present invention, preferably determined in accordance with such factors as the size of lead paddle 26 and the size of epidural space 34, lead 20 centers itself within spinal cord 30 through the action of pivot member 24 balancing itself positionally in respect of bony spinal canal 46. Pivot member 24 acts as a stabilizing element so that lead paddle 26 is optimally centered in a desired position in respect of spinal cord 30.

Figure 2:
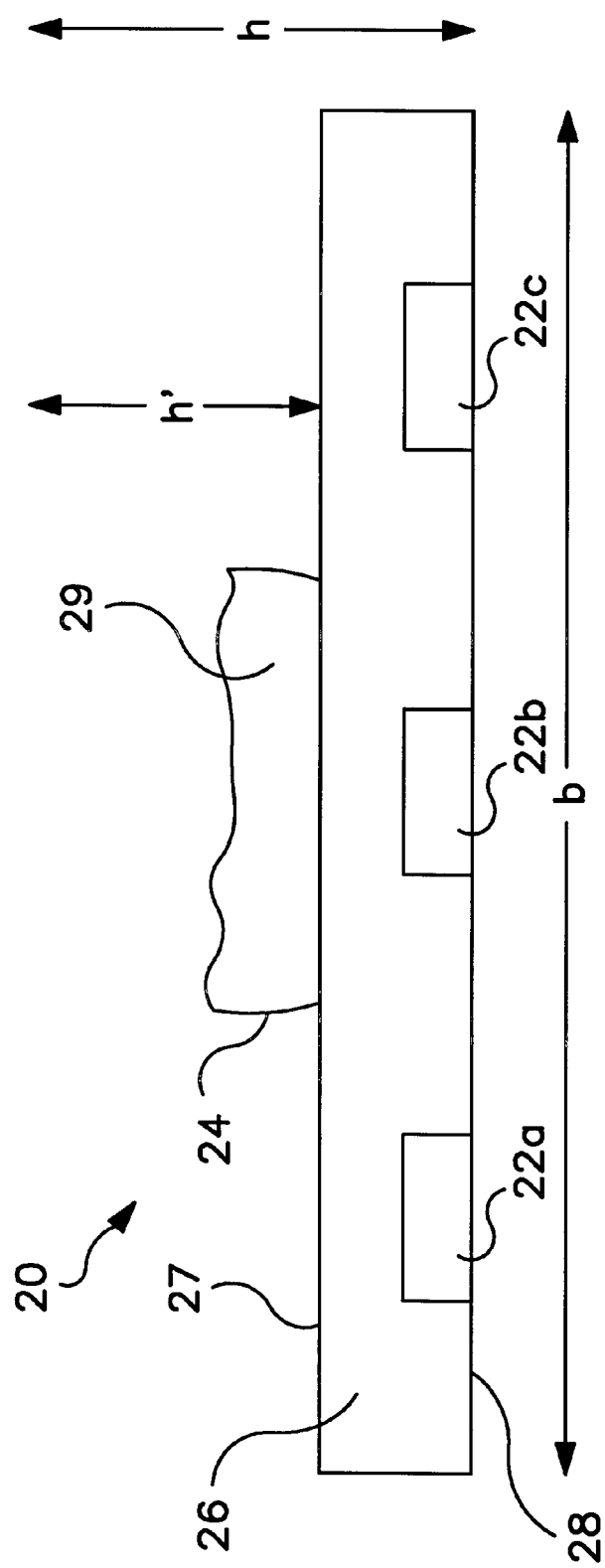
FIG. 2 is a sectional view of a second embodiment of a self-centering epidural lead in an uninflated state.

Inflatable member 29 of such an embodiment has two primary states: inflated and uninflated. Inflatable member 29 may also be partially inflated according to some embodiments of the present invention. The uninflated state is illustrated in FIG. 2: one embodiment of the inflated state is shown in FIG. 1 and pivot member 24. The shape of the inflatable member 29, however, may be of any suitable configuration required to achieve the centering function. Inflatable member 29 is preferably attached to a center region of back side 27 of lead paddle 26.

Inflatable member 29 may be completely deflated or partially inflated, and may be all or part of pivot member 24. Inflatable member 29 may be made of material such as silicon rubber although other biocompatible material may be used. Inflatable member 29 may be attached to a center region of back side 27 of lead paddle 26 using biocompatible fastening means such as those described above. Inflatable member 29 may be formed integrally with lead paddle 26. Inflatable member 29 may also comprise a sheet of such material as silicon rubber covering the back side 27 of lead paddle 26 and configured to permit the center region to be inflated as shown in FIG. 5, for example. Other configurations of inflatable member 29 are possible. For example, another possible rectangular-cross section configuration is shown in FIG. 6.

In the embodiment of the present invention shown in FIG. 2, inflatable member 29 is preferably in a partially or completely deflated state prior to lead 20 being implanted within a patient's body. Lead 20 is then inserted into epidural space 34 using existing tools and techniques for the insertion of leads as described above. Although lead 20 may be inserted in other areas, lead 20 is preferably implanted near the dorsal surface of spinal cord 30 adjacent dura mater 38. In an even more preferred embodiment of the present invention, lead 20 is implanted so that central electrode 22b faces midline M of spinal cord 30 and lead paddle 26 is centered in epidural space 34 between spinal cord 30 and bony spinal canal 46.

After lead 20 is implanted at an optimal site within epidural space 34, a suitable fluid may inserted into inflatable member 29. The fluid is preferably a hardening agent that is inserted by injection means, although other means of insertion are possible. The hardening agent is preferably an agent that hardens within 1 to 10 minutes such as, silicon rubber. Other hardening agents may also be used.

Next inflatable member 29 is inflated. Inflation preferably occurs with complete filling of the inflatable member by the hardening agent. However, inflation by other means such as partial filling of the inflatable member with a liquid hardening agent and partial filling with other fluid or material, for example, air, is contemplated in the present invention.

Inflatable member 29 is then allowed to harden within epidural space 34 of each individual patient. It is preferred that inflatable member 29 maintain some degree of flexibility or malleability following hardening. The shape in which member 29 hardens uniquely conforms within epidural space 34 of each patient. Such unique contouring to epidural space 34 of each patient helps prevent lead migration in patients having asymmetrical positioning of leads or asymmetric shape of spinal cord 30.

Hardened inflatable member 29 serves as pivot member 24 at the back end of lead paddle 26 in accordance with the embodiment of the present invention shown in FIG. 1. Pivot member 24 also causes lead 20 to balance itself against dura matter 38. In a preferred embodiment of the present invention, lead 20 includes center electrode 22b that maintains contact against dura matter 38, where contact is maintained even if the patient moves or has poor posture. Some electrodes of the prior art, provide effective stimulation only when the patient lies still. However, with lead 20 of the present invention, hardened inflatable member 29 is optimally configured to balance and position itself within epidural space 34 of an individual patient. Other lead stabilizing features may be used to prevent lead paddle 26 from further displacement.

Lead 20 maybe employed in a variety of stimulation systems. Referring to FIG. 4, for example, in one system of the present invention, a drive signal is transmitted to conventional stimulation electrodes 22a, 22b and 22c located within lead paddle 26 over conductors 23a, 23b and 23c. Conductors 23a, 23b and 23c may be located inside lead paddle 26 and may exit the skin of the patient in whom lead 20 is implanted. Although lead paddle 26 may contain fewer or more stimulation electrodes, a preferred embodiment of lead 20 of the present invention incorporates three electrodes as illustrated in FIG. 1 and FIG. 4 (in shadow). Lead 20 may also have fewer or more electrodes than three electrodes 22a–22c shown in FIGS. 1 and 4. As with lead paddle 26, electrodes 22a–22c and electrodes 23a–23c are preferably constructed of a biostable, biocompatible material that is particularly configured for long-term implantation within the human body.

Electrodes 22a–22c may be constructed so that an anode/cathode relationship is established between electrodes 22a–22c. For example, electrodes 22a and 22c may be configured as anodes (+) and electrode 22b may be configured as a cathode (−). Electrodes 22a–22c are placed on the lead in a generally planar configuration. Other arrangements of the electrode system of the present invention are possible.

Although the surface area of stimulation electrodes 22a, 22b and 22c located within lead paddle 26 may be approximately 12 mm$^2$ (a size that has been approved by the United States Federal Drug Administration), other electrode sizes and surface areas are possible. Moreover, electrode separation should be configured to have an optimal value related to the distance or separation between dura matter 38 and spinal cord 30. This optimal distance has been described extensively in the scientific literature In a preferred embodiment of lead 20 of the present invention, electrode 22b has a median position while electrodes 22a and 22c have lateral positions with respect to the spinal cord. Such an arrangement of electrodes within lead 20 allows directed or steered pulsing of the stimulation signals in the spinal cord similar to the methods and devices described in U.S. Pat. Nos. 5,643,330 and 5,501,703 to Holsheimer et al., the disclosures of which are being incorporated by reference herein, each in its respective entirety.

Furthermore, the directional nature of lead 20 in one preferred embodiment of the present invention provides for electrical contact on one side only of lead paddle 26. Electrodes 22a–22c may be disposed on lead paddle 26 in a generally planar configuration. Such an arrangement of electrodes 22a–22c requires less current to achieve the current density required to effect appropriate stimulation of the target structures of the spinal cord than does an omnidirectional cylindrical electrode, for example.

Pivot member 24 of lead 20 of the present invention enables lead paddle 26 to return to spinal midline M even after spatial lead migration has occurred. Even if pivot member 24 is pre-hardened prior to implantation, pivot member 24 centers over midline M. In an alternative embodiment of the present invention, pivot member 24 is an inflatable member 29 that hardens after implantation and which overcomes inappropriate positioning during surgery. Furthermore, in this alternative embodiment of the present invention and because inflatable member 29 may harden within the patient's body, pivot member 24 conforms appropriately to the contour of the patient's spinal cord, no matter how asymmetrical the position might be.

FIG. 4 is a rear view of one embodiment of self-centering lead 20 of the present invention. Also shown is subdural space 36 located beneath dura mater 38. Lead 20 may be used in a chronically implanted stimulation system. Alternatively, lead 20 may be used in other stimulation systems.

As shown in FIG. 4, lead paddle 26 may include an ultrasonic transducer shown schematically at 12 capable of radiating ultrasonic sound waves provided by ultrasonic drive circuit 14 over conductors 23a–23c. Alternatively, transducer 12 may be separate from paddle 26. Lead paddle 26 may further be connected to a conventional ultrasonic receiver transducer 15.

Optimal paresthesia effects using lead 20 are obtained at optimal distance D shown in FIG. 3. Generally, distance D is the point where center contact 22b of lead 20 is located an optimal distance from physiological midline M of spinal cord 30.

In one embodiment of the present invention, distance D is such that electrode 22b is about 1 mm from the midline M of the spinal cord 30. The actual optimal distance D is determined within an individual patient and is well described in the scientific literature. Distance D has also been shown to be about 2–3 mm from midline M.

Lead 20 is inserted such that the back side 27 of paddle 26 faces away from cord 30 and front side end 28 faces cord 30. Pivot member 24 extends towards the wall of the bony spinal canal 46. At the time of implantation, lead 20 may be positioned relatively easily to attain optimal distance D; the lead 20 is simply placed at the midline M of spinal cord 30 by the surgeon. However, bony spinal canal 46 in one person may have a slightly different shape in comparison to that of another person. It is such individualized shapes and the sheer boniness of the spinal canal that contributes to the spatial migration of conventional leads over time. Lead migration occurring in the first two or three weeks following lead implant surgery often destroys the optimal distance D.

Figure 7:
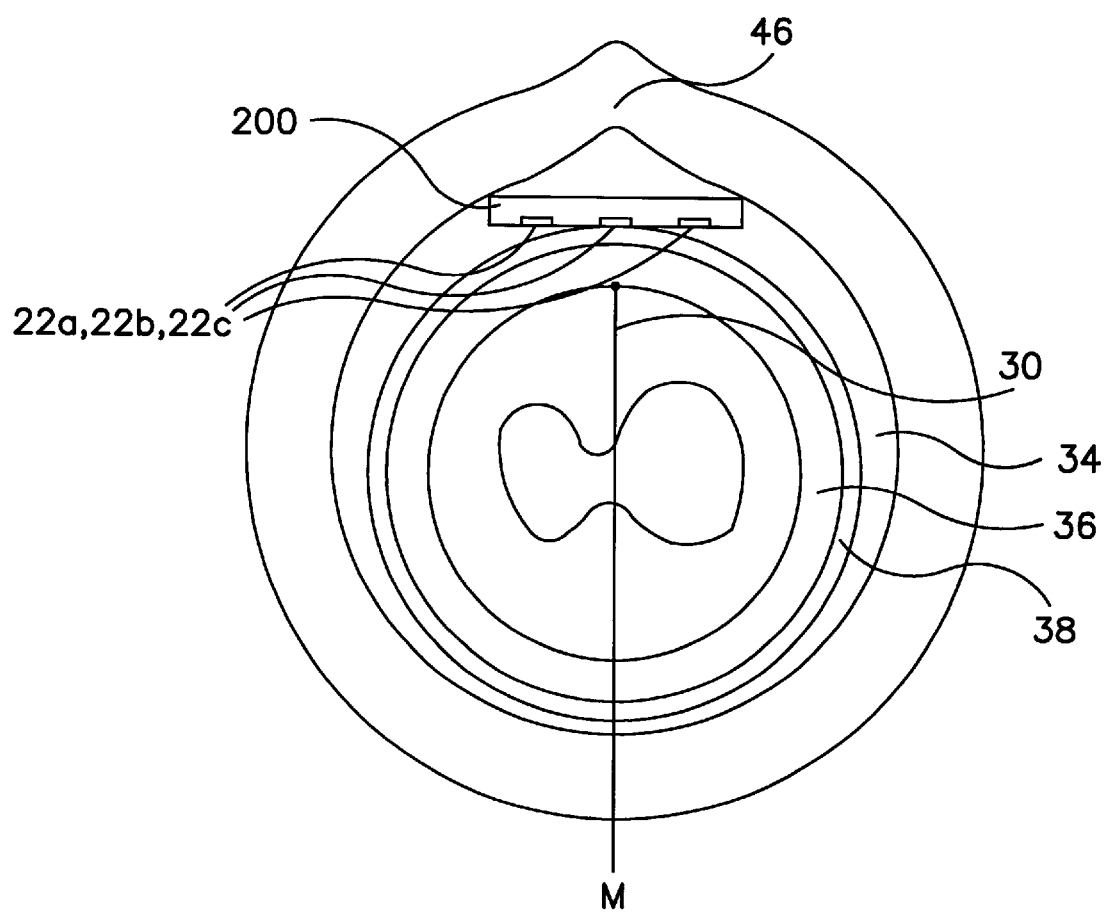
FIGS. 7 and 8 are two cross-sectional views of the vertebral canal showing implantation of a prior art lead positioned near the epidural space.
Figure 8:
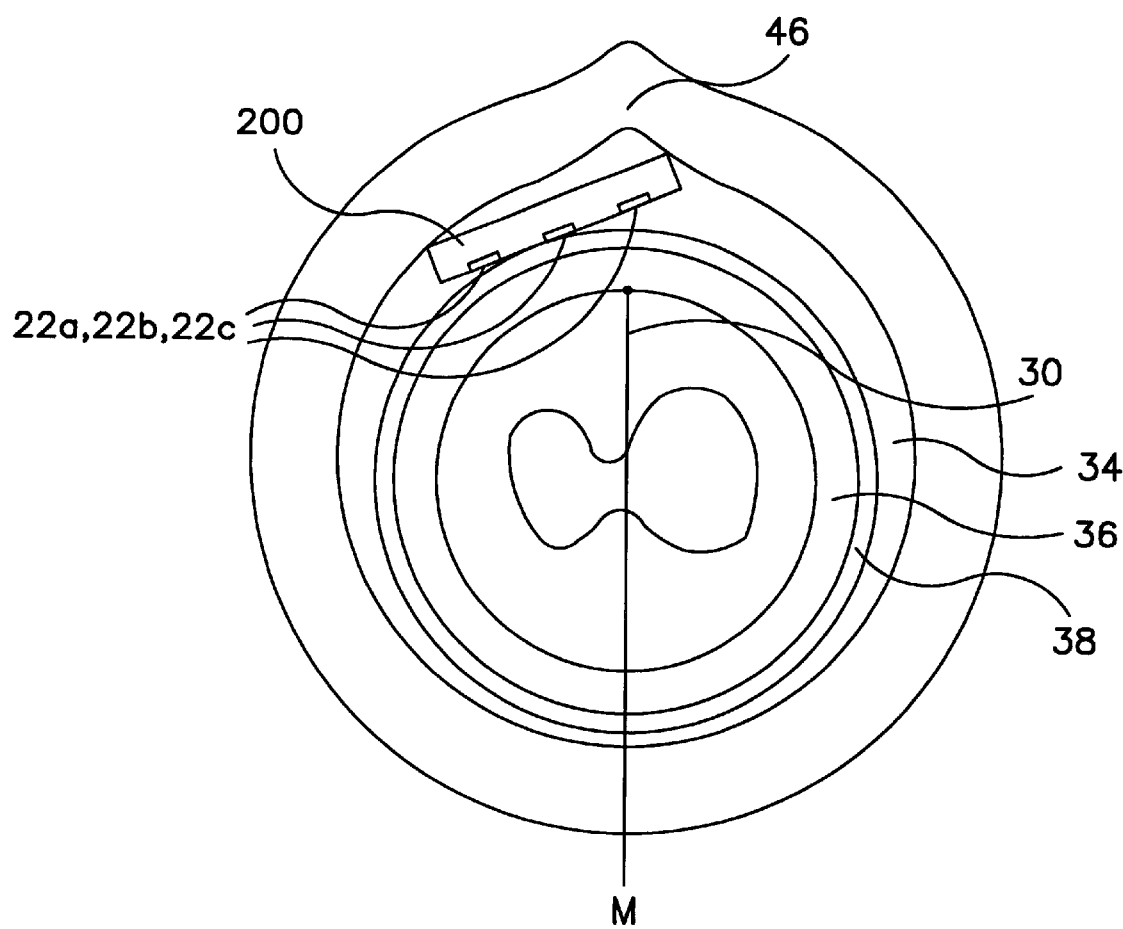

For example, FIGS. 7 and 8 show cross-sectional views of spinal cord 30 with paddle-like lead 200 implanted at midline M within epidural space 34. FIGS. 7 and 8 illustrate how lead 200 may easily migrate spatially from the initial implant position of FIG. 7 to a different position in FIG. 8 within epidural space 34. Such lead displacement may destroy the stimulation conditions required for peak efficacy, namely that lead 20 be centered over spinal cord 30 at optimal distance D.

Lead 20 therefore is well suited for use in conjunction with systems capable of changing the depth and location of stimulation patterns where the amplitude or timing of one electrical stimulation field is changed with respect to another. See, for example, the Hoslheimer patents described hereinabove. Such systems of the present invention function at peak efficacy with paddle like leads centered over midline M of spinal cord 30. Because pivot member 24 causes lead 20 to self-center, the arrangement of electrodes 22a–22c is maintained in lead 20 at the initial position that contact was first established between midline M of spinal cord 30 and electrodes 22a–22c.

Methods of making and using the foregoing self-centering epidural spinal cord stimulation lead also fall within the scope of the present invention.

All patents cited hereinabove are hereby incorporated by reference into the specification hereof, each in its respective entirety.

In the claims, means-plus-function clauses are intended to cover the structures described herein as performing the recited function and not only structural equivalents but also equivalent structures. Thus, although surgical glue and a screw may not be structurally similar in that surgical glue employs chemical bonds to fasten biocompatible components together, whereas a screw employs a helical surface, in the environment of fastening means, surgical glue and a screw are equivalent structures.

Although specific embodiments of the invention have been set forth herein in some detail, it is to be understood that this has been done for the purposes of illustration only, and is not to be taken as a limitation on the scope of the invention as defined in the appended claims. Thus, the present invention not only includes within its scope devices and methods corresponding to the pivot member and inflatable member disclosed explicitly herein, but also includes within its scope other means for self-centering now made apparent to those skilled in the art through the techniques set forth herein. It is to be understood that various alternatives, substitutions and modifications may be made to the embodiment describe herein without departing from the spirit and scope of the appended claims.

I claim:

1. A self-centering epidural spinal cord lead, comprising:

a lead including a front side and a back side, the front side being configured to face a spinal cord, and a pivot member operably attached to a center region of the back side of the lead, the pivot member comprising an inflatable member, the pivot member being configured to stabilize the lead when implanted adjacent the spinal cord, wherein the inflatable member is adapted to be injected with a hardening agent and the hardening agent is silicon rubber.

* * * * *